United States Patent [19]

Umezawa et al.

[11] 4,102,999
[45] Jul. 25, 1978

[54] PROCESS FOR PRODUCING STABLE MACROMOMYCIN POWDER

[75] Inventors: Hamao Umezawa; Tomio Takeuchi, both of Tokyo, Japan

[73] Assignee: Zaidan Hojin Biseibutsu Kagaku Kenkyu Kai, Tokyo, Japan

[21] Appl. No.: 802,348

[22] Filed: Jun. 1, 1977

Related U.S. Application Data

[63] Continuation of Ser. No. 653,873, Jan. 30, 1976, abandoned.

[30] Foreign Application Priority Data

Feb. 10, 1975 [JP] Japan .................................. 50-17163

[51] Int. Cl.² ............................................. A61K 35/00
[52] U.S. Cl. ..................................... 424/123; 424/117
[58] Field of Search .................................. 424/123, 117

[56] References Cited

U.S. PATENT DOCUMENTS 3,595,954  7/1971  Umezawa et al. .................... 424/117

OTHER PUBLICATIONS

Chimura et al., Journal of Antibiotics, vol. 21, No. 1, Jan. 1968, pp. 44–49.
Yamashita et al., Journal of Antibiotics, 29 (4), Apr. 1976, pp. 415–423.

Primary Examiner—Albert T. Meyers
Assistant Examiner—Daren M. Stephens
Attorney, Agent, or Firm—Herbert W. Taylor, Jr.

[57] ABSTRACT

There is provided a process for producing a stable macromomycin (hereinafter often referred to as MCR) powder which comprises adding a stabilizer selected from the group consisting of saccharides, amino acids and salts thereof, organic acid salts, inorganic acid salts and a chelating agent to a solution of macromomycin purified from fermentation broth prior to dehydration as by lyophilization.

15 Claims, 2 Drawing Figures

Time Course of Thermal Inactivation of MCR Lyophilized with Maltose

Arrhenius Plots of MCR Lyophilized with Maltose

PROCESS FOR PRODUCING STABLE MACROMOMYCIN POWDER

CROSS REFERENCE TO RELATED APPLICATION

This application is a continuation of our prior, co-pending application Ser. No. 653,873 filed Jan. 30, 1976, 1976 now abandoned.

BACKGROUND OF THE INVENTION

1. Field of the Invention

The purpose of the present invention is to protect the antibiotic macromomycin from inactivation during lyophilization and to enable long-term storage of macromomycin powder without inactivation.

2. Description of the Prior Art

Macromomycin was found in a culture filtrate of *Streptomyces macromomyceticus* n. sp. as an antitumor antibiotic exhibiting strong inhibition against the growth of tumor and tumor cells. It also inhibits some Gram-positive bacteria. See U.S. Pat. No. 3,595,954 and Journal of Antibiotics, 21(1), 44–49 (1968). This antibiotic has been described as an acidic, water-soluble polypeptide having a molecular weight of about 15,000. Further examination of the molecular weight in detail suggests that it is about 12,000. Macromomycin is, however, unstable, partially inactivated during lyophilization and the activity decreases even at room temperature. For example, it is difficult to store macromomycin powder without decrease of the activity in 1 or 2 months even at 5° C. Therefore, it has been very difficult to prepare pure macromomycin powder which retains high activity for a long period of time.

SUMMARY OF THE INVENTION

The present inventors have searched for effective stabilizers for MCR and found some saccharides, amino acids and salts thereof, organic acid salts, inorganic acid salts and a chelating agent such as EDTA-sodium salt are effective in stabilizing MCR.

The activity of MCR is measured by the following microbial assay method:

Method A

MCR powder is dissolved in 0.1M citric acid phosphate buffer (pH 7.0) and solutions containing 500 mcg. and 125 mcg. of MCR per ml. are prepared. The method of determining the activity described in U.S. Pat. No. 3,595,954 according to the cylinder agar plate method can be used. *Micrococcus flavus* FDA16 is used as the test organism. The medium for agar plate contains 0.6% peptone, 0.4% casamino acid, 0.15% meat extract, 0.1% glucose, 0.3% yeast extract and 1.5% agar and is adjusted to pH 7.0. The test organism is inoculated into 10 ml. of medium containing 1% meat extract, 2% glucose, 1% peptone and 0.3% sodium chloride in a test tube of 70 ml. volume and incubated at 33° C. for 15 to 24 hours. About 0.5 ml. of the cultured broth thus obtained is inoculated to 100 ml. of agar plate medium.

Method B

MCR powder is dissolved in 0.1M phosphate buffer (pH 7.0) and solutions containing 500 mcg. and 125 mcg. of MCR per ml. are prepared. The activity is measured by a cylinder agar plate method using *Sarcina lutea* ATCC 9341 as the test organism. The medium for agar plate contains 0.6% peptone, 0.3% yeast extract, 0.15% meat extract, 0.1% glucose and 1.5% agar and is adjusted to pH 6.5 The test organism is grown in a medium containing 1.0% peptone, 0.5% meat extract and 0.25% sodium chloride by incubation at 33° C. for 15 to 24 hours. About 0.5 ml. of the cultured broth is added to 100 ml. of agar plate medium and the agar plate is prepared.

The effects of saccharides in stabilizing MCR are shown in Table 1. Table 1 demonstrates that some effective compounds are found among monosaccharides, monosaccharide derivatives, disaccharides, oligosaccharides and polysaccharides. Especially disaccharides such as maltose, lactose, sucrose, cellobiose and melibiose exhibit remarkable stabilizing effects. When the ratio of saccharides to MCR in solution is at least 1:10, the effectiveness can be detected. In the case of maltose, lactose and sucrose, as shown in Table 2, the amount to be added is preferably at least about ten times, most preferably from about 20 to 80 times, the amount of MCR.

A solution containing MCR and maltose in a ratio of 1:39 was prepared by mixing together one part MCR and 39 parts maltose in water to form a solution, adjusting the pH to 5.0–7.5 and lyophilizing in a vial below 50° C. in a dark room. The present inventors have found that macromomycin is photosensitive and the procedure of lyophilization should be done in the dark. The MCR powder thus lyophilized with maltose was left to stand at 35°, 45° and 50° C. for 3, 6, 9, 12 and 15 days. The activity of each sample was measured by Method B described above and the residual activity was determined and compared to the control (0 day) which was tested immediately.

TABLE 1

| Effect of Saccharide on the Stability of MCR | |
|---|---|
| Saccharide | Residual Activity (%) |
| None | 28.3 |
| Glucose | 46.5 |
| Mannose | 45.2 |
| Galactose | 38.9 |
| Fructose | 37.1 |
| Sorbose | 40.0 |
| Mannitol | 43.4 |
| Sorbitol | 50.1 |
| Inositol | 41.5 |
| Maltose | 92.5 |
| Lactose | 95.7 |
| Cellobiose | 83.6 |
| Melibiose | 92.3 |
| Sucrose | 88.5 |
| Raffinose | 82.2 |
| Dextrin | 45.5 |
| Dextran | 53.5 |

(a) 2 ml. of solution containing 5 mg. of MCR and 50 mg. of each saccharide was lyophilized and the samples were left to stand at 65° C. for 55 hours.

(b) The activity was measured by Method A, and per cent of the residual activity to the control was calculated.

TABLE 2

| Effect of Maltose, Lactose and Sucrose on the Stability of MCR | | |
|---|---|---|
| Saccharide | Amount of Saccharide (mg.) | Residual Activity (%) |
| None | 0 | 28.9 |
| Maltose | 5 | 82.6 |
|  | 10 | 83.8 |
|  | 20 | 88.5 |
|  | 40 | 94.9 |
|  | 80 | 96.1 |
|  | 160 | 94.2 |
| Lactose | 5 | 84.1 |
|  | 10 | 87.8 |
|  | 20 | 91.4 |

TABLE 2-continued

Effect of Maltose, Lactose and Sucrose on the Stability of MCR

| Saccharide | Amount of Saccharide (mg.) | Residual Activity (%) |
|---|---|---|
|  | 40 | 94.5 |
|  | 80 | 94.3 |
|  | 160 | 93.8 |
| Sucrose | 5 | 80.1 |
|  | 10 | 80.4 |
|  | 20 | 84.4 |
|  | 40 | 91.4 |
|  | 80 | 90.9 |
|  | 160 | 90.0 |

(a) 2 ml. of solution containing 2 mg. of MCR and varied amount of each saccharide was lyophilized in a vial. Samples were left to stand at 50° C. for four days.

(b) The activity was measured by Method B and percent of the residual activity to the control was obtained.

FIG. 1 shows the logarithmic plotting of residual percent of activity with respect to the days at 35°, 45° and 50° C.

As shown in FIG. 1, the logarithms of residual activities at each temperature were on a straight line. These findings indicate that inactivation of MCR follows the first-order reaction within these temperatures. Based on the data shown in FIG. 1, the rate constant, $k$ of MCR, was calculated according to the equation (1) below.

$$k = 2.303/t \times \log C_o/C \text{ (hr}^{-1}\text{)} \tag{1}$$

$t$ : Heating period (hour).
$C_o$: Initial concentration, 100%.
$C$ : Residual percent of activity after $t$ hours.

Values of rate constants were $6.096 \times 10^{-4}$ at 50° C., $3.832 \times 10^{-4}$ at 45° C. and $1.407 \times 10^{-4}$ at 35° C. FIG. 2 shows the logarithmic plotting of rate constant ($k$) to the reciprocal of the absolute temperature ($T$).

As shown in FIG. 2, plots of log $k$ to 1/T form a substantially straight line and this result indicates that Arrhenius equation between the rate constant and absolute temperature can be applied. Therefore according to the Arrhenius equation, the periods for retaining at least 90% of activity of the MCR powder at various temperatures were calculated. As a result of such calculations, it was determined that MCR powder lyophilized with maltose can be stored at 4° C. for 37 months, at 10° C. for 17 months, at 25° C. for 3 months and 35° C. for 31 days. MCR powder not stabilized with maltose reduced its potency to 86% of the original at 4° C. after 3 months and lost almost all activity at 35° C. after 30 days.

Amino acids and salts thereof such as sodium L-glutamate, potassium magnesium L-aspartate, L-threonine, L-lysine hydrochloride, L-tryptophan, L-glutamine and L-asparagine were also effective in stabilizing MCR as shown in Table 3. The suitable amount of these amino acids in the solution is from about 1 to about 20 times the amount of MCR.

Organic acid salts such as sodium citrate, sodium tartrate, sodium oxalate, sodium fumarate, sodium gentisate and sodium malate and inorganic acid salts such as potassium chloride, magnesium sulfate and manganese chloride and a chelating agent such as EDTA-sodium salt were effective as stabilizers, as shown in Table 4. Suitable amounts of organic acid salt, inorganic acid salt and EDTA-sodium salt are in the range from about 0.5 to about 10 times, from about 0.01 to about equal and from about 0.001 to about 0.1 times the amount of MCR, respectively.

As shown in Table 5, the combined addition of two or more stabilizers which showed effectiveness for stabilization of MCR appreciably enhanced the stability of the MCR powder. The amount of each stabilizer used alone may be used in the same amount when using a combination of two or more stabilizers.

TABLE 3

Effect of Amino Acids and Salts Thereof on the Stability of MCR

| Amino Acid | Residual Activity (%) |
|---|---|
| None | 24.1 |
| Sodium L-glutamate | 64.9 |
| Potassium Magnesium l-aspartate | 76.3 |
| L-Threonine | 53.9 |
| L-Lysine hydrochloride | 52.6 |
| L-Tryptophan | 65.8 |
| L-Glutamine | 48.7 |
| L-Asparagine | 53.9 |
| L-Glycine | 43.4 |
| L-Proline | 32.0 |
| L-Histidine hydrochloride | 23.2 |

(a) 2 ml. of solution containing 10 mg. of MCR and 100 mg. of each amino acid was placed in a vial, adjusted to pH 5.0–7.5 and lyophilized.

(b) Methods, other than (a) are described in Table 1.

TABLE 4

Effect of Organic Acid Salts, Inorganic Acid Salts and EDTA-sodium Salt on the Stability of MCR

| Stabilizer | Amount of Addition (mg.) | Residual Activity (%) |
|---|---|---|
| None | 0 | 24.1 |
| Sodium citrate | 100 | 74.0 |
| Sodium tartrate | 100 | 72.0 |
| Sodium oxalate | 100 | 53.9 |
| Sodium fumarate | 100 | 55.4 |
| Sodium gentisate | 100 | 68.5 |
| Sodium malate | 100 | 56.2 |
| Magnesium sulfate . 7 $H_2O$ | 1 | 50.2 |
| Manganese chloride . 4 $H_2O$ | 1 | 48.9 |
| Potassium chloride | 1 | 53.8 |
| Monobasic sodium phosphate . 2 $H_2O$ and dibasic sodium phosphate. 12 $H_2O$ | 1 and 3 | 58.1 |
| EDTA-disodium salt | 0.1 | 67.0 |

(a) 2 ml. of solution containing 10 mg. of MCR and amounts of stabilizers shown in the table was placed in a vial and lyophilized.

(b) Methods other than (a) are described in Table 1.

TABLE 5

Combined Effect of Two Stabilizers on the Stability of MCR

| Stabilizer | Residual Activity (%) |
|---|---|
| None | 25.0 |
| Lactose 100 mg/2ml. | 94.3 |
| Lactose + Sodium citrate (mg/2ml) (100 mg./2 ml.) |  |
| 0.1 | 93.8 |
| 0.4 | 96.1 |
| 1.6 | 98.0 |
| 6.4 | 98.5 |
| 29.6 | 98.3 |
| Lactose + EDTA-disodium salt (mg/2ml) (100 mg./2 ml.) |  |
| 0.02 | 97.7 |
| 0.08 | 98.7 |
| 0.32 | 95.4 |
| 1.28 | 90.5 |

TABLE 5-continued

Combined Effect of Two Stabilizers on the Stability of MCR

| Stabilizer | Residual Activity (%) |
|---|---|
| 5.12 | 85.5 |

(a) Total volume in a vial is 2 ml. and 10 mg. of MCR is contained in a vial.

(b) Methods other than (a) are described in Table 1.

The following examples are illustrative of the present invention and are not intended to limit the scope thereof.

DESCRIPTION OF THE PREFERRED EMBODIMENTS

Example 1

Figure 1:
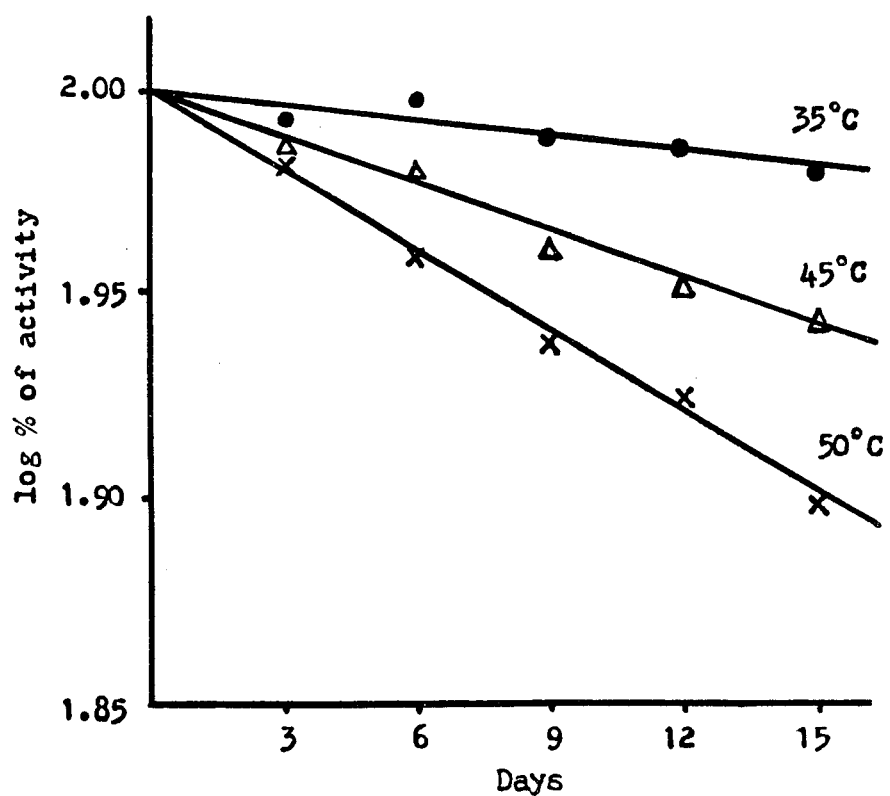
Figure 2:
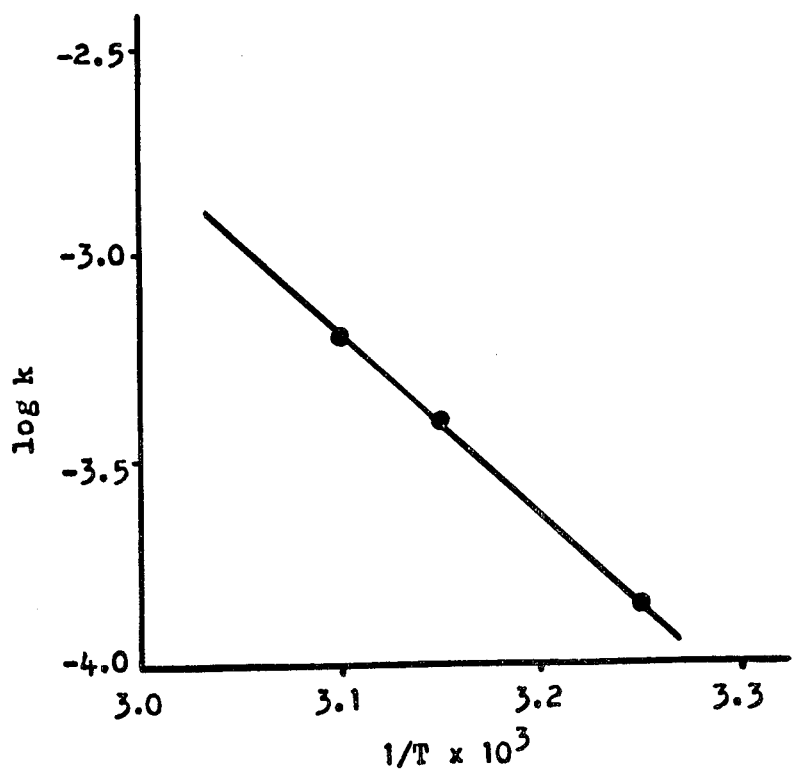

(a) An initial solution was prepared by dissolving 100 mg. of MCR and 1,000 mg. of lactose in 20 ml. of water. Five samples were prepared by placing 2 ml. of the initial solution into each of 5 vials and lyophilized to form a powder.

(b) Five control samples were prepared in a manner substantially the same as in (a) above except that the lactose was omitted.

The samples as prepared above were sealed and left to stand at 65° C. for 1 and 3 days and at 45° C. for 8 and 16 days. Tests for residual activity were conducted on each sample including one sample of (a) and one of (b) which were tested immediately after preparation, i.e. tested at 0 days. The measurement of activity of MCR was made in accordance with Method A, i.e. the cylinder agar plate method using *Micrococcus flavus* as the test organism. Residual activity was determined regarding activity before lyophilization as 100% and the results are shown in Table 6.

TABLE 6

| Stabilizer | 0 Day | Residual Activity of MCR | | | |
|---|---|---|---|---|---|
| | | 65° C. | | 45° C. | |
| | | 1 Day | 3 Days | 8 Days | 16 Days |
| None | 90.0% | 22.3% | 13.5% | 19.5% | 12.5% |
| Lactose | 99.1 | 97.0 | 94.7 | 96.5 | 92.2 |

Example 2

(a) An initial solution was prepared by dissolving 20 mg. of MCR and 780 mg. of maltose in 20 ml. of water. Five samples were prepared by placing 2 ml. of the initial solution into each of 5 vials and lyophilized to form a powder.

(b) Five control samples were prepared in a manner substantially the same as in (a) above except that the maltose was omitted.

The samples as prepared above were sealed and left to stand at 35° C. for 5, 10, 20 and 30 days. The activity of each sample was measured by Method B, i.e. the cylinder agar plate method using *Sarcina lutea* as the test organism. Residual activity was determined regarding activity before lyophilization as 100%, and the results are shown in Table 7.

TABLE 7

| Days | Residual Activity of MCR | |
|---|---|---|
| | Without Maltose | With Maltose |
| 0 | 86.8% | 98.4% |
| 5 | 59.9 | 97.3 |
| 10 | 22.6 | 96.8 |
| 20 | trace | 94.9 |
| 30 | trace | 91.2 |

While the described embodiments represents the preferred forms of the present invention, it is to be understood that modifications will occur to those skilled in the art without departing from the spirit of the invention.

We claim:

1. A process for producing stable macromomycin powder which comprises (a) forming a solution by mixing in an aqueous medium one part by weight of solid macromomycin and at least 10 parts by weight of a stabilizer selected from the group consisting of maltose, lactose, sucrose, cellobiose, melibiose and raffinose and (b) dehydrating the resulting solution to form a powder.

2. The process according to claim 1 wherein the weight of the stabilizer employed is from about 20 to about 80 times the weight of macromomycin in the solution.

3. The process according to claim 1 wherein the pH of the solution containing macromomycin and the stabilizer is adjusted to a range of from 5.0 to 7.5.

4. The process according to claim 1 wherein the temperature during the dehydration step is kept below 50° C.

5. The process according to claim 1 wherein dehydration is by lyophilization.

6. A process for producing stable macromomycin powder which comprises (a) forming a solution by mixing in an aqueous medium one part by weight of solid macromomycin and at least ten parts by weight of maltose as a stabilizer and (b) dehydrating the resulting solution to form a powder.

7. The process according to claim 6 wherein the weight of the stabilizer employed is from about 20 to about 80 times the weight of macromomycin in the solution.

8. The process according to claim 6 wherein the pH of the solution containing macromomycin and the stabilizer is adjusted to a range of from 5.0 to 7.5.

9. The process according to claim 6 wherein the temperature during the dehydration step is kept below 50° C.

10. The process according to claim 6 wherein dehydration is by lyophilization.

11. A process for producing stable macromomycin powder which comprises (a) forming a solution by mixing in an aqueous medium one part by weight of solid macromomycin and at least ten parts by weight of a lactose and a stabilizer and (b) dehydrating the resulting solution to form a powder.

12. The process according to claim 11 wherein the weight of the stabilizer employed is from about 20 to about 80 times the weight of macromomycin in the solution.

13. The process according to claim 11 wherein the pH of the solution containing macromomycin and the stabilizer is adjusted to a range of from 5.0 to 7.5.

14. The process according to claim 11 wherein the temperature during the dehydration step is kept below 50° C.

15. The process according to claim 11 wherein dehydration is by lyophilization.

* * * * *